US010509014B2

(12) United States Patent
Segall

(10) Patent No.: US 10,509,014 B2
(45) Date of Patent: Dec. 17, 2019

(54) METHOD AND DEVICE FOR THE TESTING OF ULTRASOUND PROBES

(71) Applicant: BBS Försäljnings AB, Vätö (SE)

(72) Inventor: Björn Segall, Vätö (SE)

(73) Assignee: BBS FÖRSÄLININGS AB, VÄTÖ (SE)

( * ) Notice: Subject to any disclaimer, the term of this patent is extended or adjusted under 35 U.S.C. 154(b) by 0 days.

(21) Appl. No.: 15/119,836

(22) PCT Filed: Feb. 19, 2015

(86) PCT No.: PCT/EP2015/053512
§ 371 (c)(1),
(2) Date: Aug. 18, 2016

(87) PCT Pub. No.: WO2015/124675
PCT Pub. Date: Aug. 27, 2015

(65) Prior Publication Data
US 2017/0067858 A1    Mar. 9, 2017

(30) Foreign Application Priority Data

Feb. 19, 2014  (SE) ...................................... 1450203

(51) Int. Cl.
*G01N 29/30* (2006.01)
*A61B 8/00* (2006.01)
(Continued)

(52) U.S. Cl.
CPC ........... *G01N 29/30* (2013.01); *A61B 8/4444* (2013.01); *A61B 8/4494* (2013.01); *A61B 8/461* (2013.01);
(Continued)

(58) Field of Classification Search
CPC .... G01N 29/30; A61B 8/4444; A61B 8/4494; A61B 8/461; A61B 8/54; A61B 8/56; A61B 8/58
See application file for complete search history.

(56) References Cited

U.S. PATENT DOCUMENTS 4,070,905 A   1/1978  Kossoff
4,183,249 A   1/1980  Anderson
(Continued)

FOREIGN PATENT DOCUMENTS

EP    2253968 A2    11/2010

OTHER PUBLICATIONS

International Search Report from corresponding International Application No. PCT/EP2015/053512, dated Apr. 21, 2015.
(Continued)

*Primary Examiner* — David Z Huang
(74) *Attorney, Agent, or Firm* — Tucker Ellis LLP

(57) ABSTRACT

There is provided a device for testing ultrasound probes comprising a plurality of transducing elements, said device comprising a plurality of ultrasound transmitter/receiver circuits, a computing device and a control device arranged to control the transmitter/receiver circuits and the computing device arranged to select an interrogation protocol from a plurality of different interrogation protocols, where each interrogation protocol comprises instructions for the order in which the plurality of transmitter/receiver circuits shall send voltage pulses to the transducers of the ultrasound probe.

4 Claims, 7 Drawing Sheets

(51) Int. Cl.
 *B06B 1/02* (2006.01)
 *G01N 29/26* (2006.01)
 *A61B 8/08* (2006.01)

(52) U.S. Cl.
 CPC ............... *A61B 8/488* (2013.01); *A61B 8/54* (2013.01); *A61B 8/56* (2013.01); *A61B 8/58* (2013.01); *A61B 8/587* (2013.01); *B06B 1/0215* (2013.01); *G01N 29/262* (2013.01); *B06B 2201/40* (2013.01); *G01N 2291/106* (2013.01)

(56) References Cited

U.S. PATENT DOCUMENTS

| | | | |
|---|---|---|---|
| 4,274,422 A | 6/1981 | Anderson et al. | |
| 4,811,740 A | 3/1989 | Ikeda | |
| 5,337,611 A * | 8/1994 | Fleming | G01N 29/0618 73/622 |
| 6,918,877 B2 * | 7/2005 | Hossack | B06B 1/0292 600/447 |
| 7,028,529 B2 | 4/2006 | Gessert et al. | |
| 2005/0243812 A1 | 11/2005 | Phelps | |
| 2011/0030448 A1 | 2/2011 | Moore | |
| 2015/0141832 A1 * | 5/2015 | Yu | A61B 8/5215 600/455 |

OTHER PUBLICATIONS

International Preliminary Report on Patentability from corresponding International Application No. PCT/EP2015/053512, dated May 4, 2016.
Tutwiler et al., "Design of a Test System to Characterize Very High-Frequency Ultrasound Transducer Arrays", vol. 3664, Feb. 25, 1999, pp. 182-193.

* cited by examiner

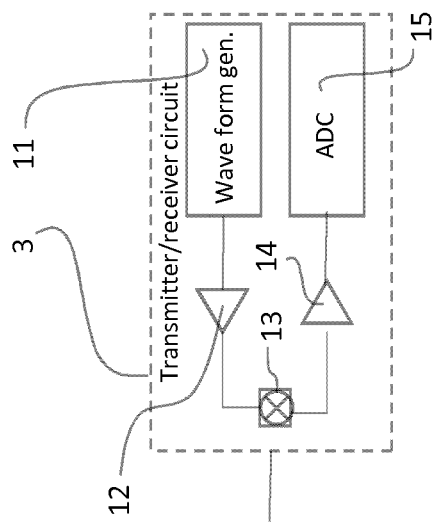
Fig. 8
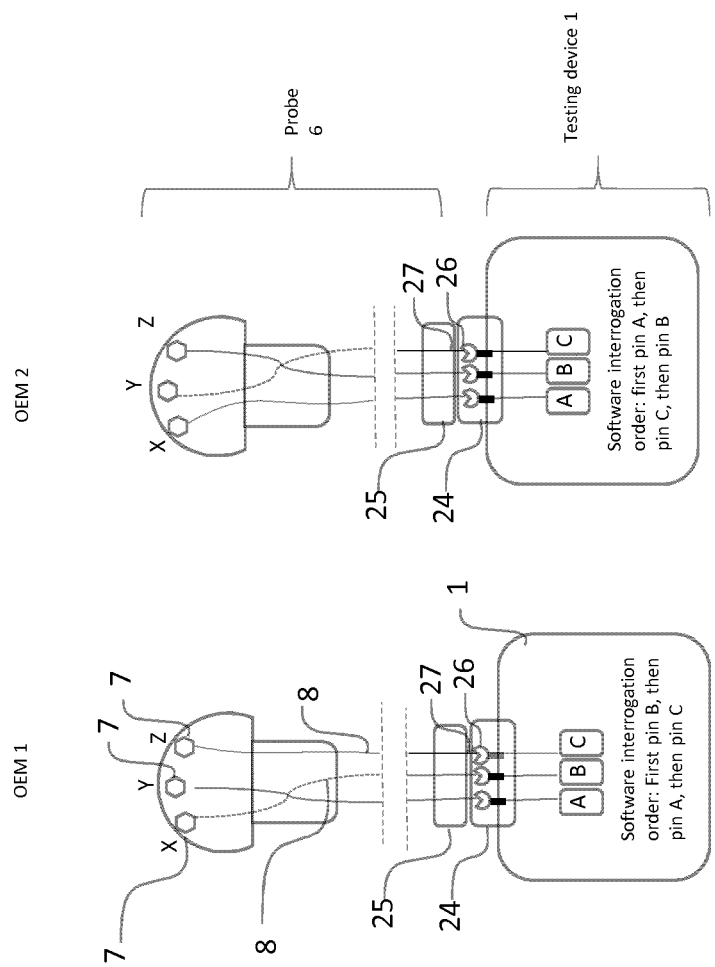
Fig. 7a
Fig. 7b

METHOD AND DEVICE FOR THE TESTING OF ULTRASOUND PROBES

FIELD OF THE INVENTION

This invention relates to a device for testing ultrasound probes.

BACKGROUND

Ultrasound is frequently used in healthcare, for example in diagnosis and for monitoring pregnancies. Ultrasound is also used for detection of structural defects for example in machinery; and for other purposes. Ultrasound technology relies on detecting the scattering of sound waves. Sending and receiving the ultrasound wave is usually carried out with a piezoelectric transducer that can generate a sound wave upon receiving a voltage pulse and generate a voltage pulse upon receiving a sound wave.

Ultrasound probes consist of a plurality of piezoelectric crystals that each are controlled by a lead capable of sending and receiving voltage pulses. Ultrasound images are generated by transforming the voltage pulses that are generated by the transducers when they receive sound echoes caused by the previously sent ultrasound waves.

An ultrasound probe comprises several transducing elements. The number of transducing elements vary from 64 to 256, or even more.

Ultrasound probes need to be tested at regular intervals to ensure that they are working properly. Tests are carried out by specialized staff that are trained in ultrasound probe testing. Ultrasound probe testers regularly visit for example hospitals to test their ultrasound probes.

Problems with the probe may include problems with the leads, crosstalk between leads and errors in the transducers such as air under the lens, detachment of the backing material of the piezoelectric crystal, detachment of the piezoelectric crystal, and the transducers changing frequency.

Different instruments have been developed to cater to the business of ultrasounds probe testing.

The ultrasound test apparatus disclosed in U.S. Pat. No. 7,028,529 has one transmitter and one receiver and can test one lead and one transducing element at a time. Thus it has only one channel and usually interrogates the transducing elements one by one, which is a slow process. A relay matrix is used to switch the transmitter/receiver to the correct transducer. An advantage with relays according to U.S. Pat. No. 7,028,529 is to limit capacitive and resistive loads. However, relays are slow and it would be desirable to have a probe testing device with faster switching capabilities.

SUMMARY OF THE INVENTION

To provide a probe testing device with faster switching capabilities it is provided a multichannel testing device.

In a first aspect of the invention it is provided a device for testing ultrasound probes comprising a plurality of transducing element/lead pairs, said device comprising a plurality of ultrasound transmitter/receiver circuits, a control device arranged to control the ultrasound transmitter/receiver circuits, said control device comprising a computing device arranged to select an interrogation protocol from a plurality of different interrogation protocols, where each interrogation protocol comprises instructions for the order in which the plurality of transmitter/receiver circuits shall send voltage pulses to the transducer element/lead pairs of the ultrasound probe. Preferably the interrogation protocols are encoded by software.

The device has several advantages. It has the advantage that it has faster switching capabilities. This makes it possible to detect crosstalk in a manner described above. Since the probe-specific information to a great extent is encoded in software and not hardware it is easier to change and to adapt, and to distribute. Furthermore, the fast switching makes enables the device to produce a real time image. This can be used to improve the diagnosis of the probe.

Preferably the device additionally comprises a video-frame capture capability capable of producing a real time image. Preferably the real time image can be updated at least 4 times per second.

Preferably the device has a number of transmitter/receiver circuits that correspond to the number of transducing elements in the probe to be tested. Most probes on the market today has 128 transducers and the device preferably has at least 128 transmitter/receiver circuits. Preferably the device has pulse repletion frequency of at least 640 Hz when there are 128 transmitter/receiver circuits.

The device may provide an image is an image that is able to show relative motion (Doppler mode imaging). This has the advantage that more specific information about the probe may be provided.

The device preferably is connectable to an adaptor, thereby achieving connectability to least two different kinds of ultrasound probes. Preferably at least two different kinds of ultrasound probes are conventional existing ultrasound probes.

This has the advantage that probes from several different manufactures can be tested with the device.

The interrogation protocol may comprise information about which type of adapter that should be connected to the device. This makes it easier for the user to select the appropriate adapter.

In a second aspect of the invention it is provided a computer-readable storage medium having computer-readable program embodied therein for directing operation of a device comprising a plurality of ultrasound transmitter/receiver circuits, a control device comprising a computing device arranged to control the transmitter/receiver circuits wherein the computer readable program includes instructions for operating the device to test an ultrasonic probe having a plurality of transducing elements in accordance with the following: a) selecting, from a plurality of interrogation protocols, one interrogation protocol for the order in which the plurality of transmitter/receiver circuits shall send voltage pulses to the transducers of the ultrasound probe, and b) sending voltage pulses from the transmitters according to the interrogation protocol, and registering voltage pulses to the receivers according to the interrogation protocol.

In a third aspect of the invention it is provided a method for testing ultrasound probes with a plurality of transducing elements and leads comprising the steps of: a) selecting, from a plurality of interrogation protocols, one interrogation protocol for the order in which a plurality of transmitter/receiver circuits shall send voltage pulses to the transducers of the ultrasound probe, b) sending voltage pulses from the transmitters according to the interrogation protocol, and registering voltage pulses to the receivers according to the interrogation protocol.

The method may comprise the additional step c) of determining at least one of the following parameters for each of the transducer element/lead pairs: capacitance, frequency, bandwidth, pulse width and relative sensitivity.

The method according may include the step of displaying information to a user about which adapter that is to be connected to the device, where said information is stored in the interrogation protocol. This makes it easier for the user to select the appropriate adapter.

The method may be adapted to detect crosstalk between the leads/and or transducers of the probe and comprises the steps of: i) selecting a first transducer element, ii) sending a voltage pulse to that transducer element, iii) registering voltage pulses to all receivers, and iv) repeating steps i)-iii) until voltage pulses have been sent to all transducers. Previously detecting crosstalk has been an extremely time-consuming procedure since the test instruments can only listen for crosstalk in one lead at a time, requiring cumbersome recursions in order to check for crosstalk between all leads and transducer elements.

BRIEF DESCRIPTION OF DRAWINGS

FIG. 7 is a schematic overview of how two different interrogation protocols can be used to test probes from two different probe manufactures.

FIG. 8 is an example of a transmitter/receiver circuit.

DETAILED DESCRIPTION

"Ultrasound probe" refers to an acoustic device having a plurality of transducing elements adapted for conversion between electric and acoustic signals and between acoustic signals and electric signals, and leads for connecting each of the transducer elements to an ultrasound machine for example an ultrasound imaging machine. Typically the transducing elements are piezoelectric crystals. The transducer element and its lead may be referred to as "transducer element/lead pair" herein.

Figure 1:
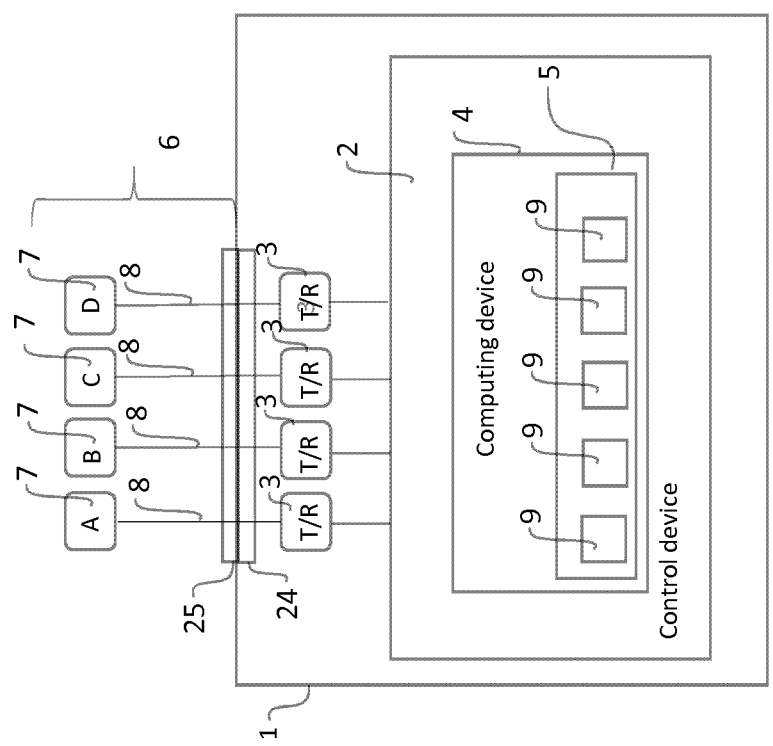
FIG. 1 is a schematic overview of the device connected to a probe.

With reference to FIG. 1, the device 1 comprises a control device 2, which controls a plurality of transmitter/receiver circuits 3 (four transmitter/receiver circuits are shown in FIG. 1). The control device comprises at least one computing device 4, which preferably can store software in a memory 5. The computing device can be any suitable computer capable of executing software, for example a mainframe, a PC or a laptop.

An example of the arrangement of the transmitter/receiver circuits is seen in FIG. 8. Each transmitter/receiver circuit 3 is suitable for generation and receipt of voltage pulses to ultrasound probes 6 with transducing elements 7. A suitable pulse can be a 40 ns square or ramped pulse with a magnitude of about 75 V, although voltage of from 1 V to 90 V can be used.

Suitably each of the transmitter/receiver circuits 3 comprises an analog to digital converter (ADC) 15 as an interface with the control device 2. It is referred to the description of FIG. 3 for more details.

The probe 6 comprises transducer elements 7, a probe connector 25 and a plurality of leads 8 between the probe connector 25 and the transducer elements 7. The plurality of leads 8 forms a cord of the probe 6.

Figure 2:
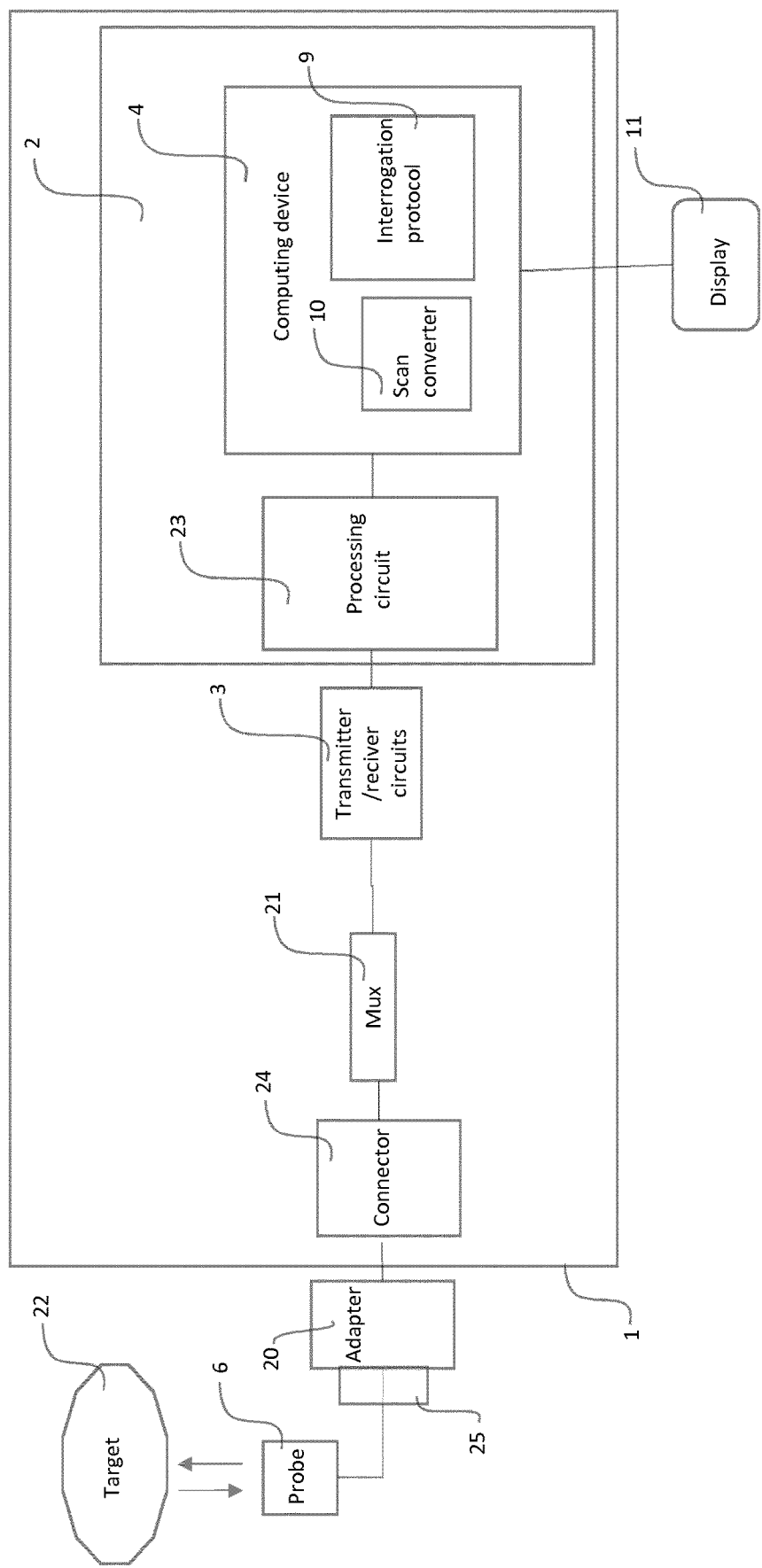
FIG. 2 is an example of an embodiment of the device.

With reference to FIG. 1 and FIG. 2, the control device 2 receives signals from the transmitter/receiver circuits 3 and sends signals to the transmitter/receiver circuits 3. The probe connector 25 of the probe 6 can be connected to connector of device 24, possibly with the aid of an adapter 20 (FIG. 2). Each transmitter/receiver circuit 3 is connected to a pin hole 26 on a connector 24 of the device 1 for receiving a contact pin 27 of probe connector 25 or adapter 20 (schematically shown in FIGS. 7a and 7b). Each contact pin 27 of probe connector 25 will then be brought in contact with a pin hole 26 and a lead in device 1 that is in contact with one transmitter/receiver 7. Herein, probe connector 25 has contact pins and connector 24 of device has pin holes. However, the situation may also be the other way around such that the probe connector 25 has pin holes and the connector 24 of device has contact pins. Control device 2 provides the necessary hardware and software to control transmitters/receivers 3 to collect and process ultrasonic echo signals. The control device 2 provides amplification, digitization, and other signal processing of the electrical signal as is understood in the art of ultrasonic imaging. The control device 2 is preferably partly semiconductor based so that it involves no moving parts. This results in fast switching.

The software of the computing device 4 includes a plurality of interrogation protocols 9. Thus there are at least two interrogation protocols. Each interrogation protocol is designed for a particular model or make of probe 6 as described herein. In particular the interrogation protocols differs in the order in which voltage pulses are sent from the plurality of transmitter/receiver circuits 3. Five different interrogation protocols 9 stored in a memory 5 of computing device 4 are shown in FIG. 1. The interrogation protocols 9 are however not necessarily stored in a memory 5 of computing device 4. However, the computing device 4 has access to the interrogation protocols 9. The interrogation protocols 9 can also be accessed from an external memory, such as a server which is accessed through a network. The interrogation protocol 9 can be available in any suitable file format.

The device 1 is connectable to an ultrasonic probe 6 to be tested comprising transducer elements 7 and leads 8 for conducting voltage pulses to and from transducer elements 7.

The device 1 can test the probe 6 in different ways. The device 1 is preferably capable of switching between at least two test modes, a transducer interrogation mode and an image mode. The image mode enables the device to create an ultrasonic image by methods known in the art.

In the transducer interrogation mode, the probe 6 is tested by device 1 by sending a voltage pulse to one of the transducer elements 7 at a time to test the transducer elements 7 and the leads 8 individually. This is referred to as "transducer interrogation". This testing can be done with methods known in the art. For example, one useful method to test the leads 8 of the probe 6 is to measure the capacitance of each of the leads 8 by sending a voltage pulse. A lower than expected capacitance indicates a break in the lead 8 whereas a higher than expected capacitance could indicate a short circuit. As described below, crosstalk between leads 8 can also be tested. The transducer elements 7 can also be tested in various ways. For example, the bandwidth of the frequency for each of the transducer elements 7 can be tested with methods known in the art. Other parameters that can be tested for each of the transducer elements 7 include the highest and the lowest capacitance ($\Omega$), frequency (Hz), central frequency (Hz), bandwidth (Hz), pulse width (s), and relative sensitivity. The control device 2 and computing device 4 carries out the necessary analysis of signals and computing in order to determine these parameters for each of the transducing elements 7 and leads 8. This is done on the basis of the signals sent and received by the transmitter/receiver circuits 3 as digitized by ADC 15.

Transducer interrogation is usually done for one transducer element/lead pair at a time. However, the device carries out testing extremely fast since it does not have any moving parts. In other embodiments interrogation can be carried out for all transducers simultaneously or almost simultaneously.

Testing the transducers one by one in the transducer interrogation mode is conveniently done by sending a voltage pulse from one transmitter/receiver 3 to one transducer 7 through lead 8 to create an ultrasonic pulse and reflection and receiving the voltage pulse created by the echo. The probe 6 may be arranged in the test set up such that it directed towards a phantom target 22 that creates an echo.

The probe 6 can be connected to the connector of device 24 (in FIG. 2) with a connector of probe 25 which is a part of the probe 6. Although probes from different OEMs may have the same type of physical connector the wiring may be different such that contact pin A on the connector of probe 25 is used for (connected to) transducer element Y in OEM 1 (OEM=Original Equipment Manufacturer) but that contact pin A of the connector of probe 25 is connected to transducer element X in OEM 2.

Often it is desirable to test the transducer element/lead pairs in a predetermined order. This order is often to test the transducer element/lead pairs from one end of the probe to the other (linear sequence).

Therefore the testing of probes from different manufacturers requires sending voltage pulses to the different leads in different orders for different probes. For example, for one manufacturer, signals should be sent to the transducers in the order A, B, C. For probes from another manufacturer the transducers should be activated in the order B, A, C.

FIGS. 7a and 7b illustrates how probes 6 from two probes (OEM1 and OEM2) from two different original equipment manufacturers (OEM:s) are tested in linear sequence by the device with the use of two interrogation protocols, one interrogation protocol for each probe. A B and C represent three different transmitter receiver circuits 3 that each is connected to a pin hole 26 on the connector of the device 24.

Thus, the interrogation protocol 9 determines the order of the activation of transmitter/receiver circuits 3 A, B and C, the order being adapted to a certain type of probe. In the example in FIGS. 7a and 7b the transmitter/receiver circuits 3 should be activated in the order B, A, C for OEM 1 (FIG. 7a) and in the order A, C, B for OEM 2 (FIG. 7b) in order to obtain a linear sequence of activation for transducers X, Y and Z. In prior art instruments there is only one transmitter/receiver and the switching between A, B and C is achieved with the aid of mechanical relays. The current invention has multiple transmitter/receivers which has advantages such that a real time image can be created, testing can be carried out faster and crosstalk can be tested for.

The order of activating the transducing elements 7 by device 1 is determined by an interrogation protocol 9, which consists of instructions necessary for transmitting voltage pulses from the transmitter/receiver circuits 3, thus activating the transducers 7 of a probe 6 in a certain predetermined pattern or order. The pattern can for example be that the transducers should be activated from one side of the probe to the other (linear sequence). The interrogation protocol 9 is specific for a certain type of probe 6, for example a certain model of probe from a certain manufacturer. The different interrogation protocols 9 can preferably be in the form of software files that is stored in the memory 5 of computing device 4 or accessed from a remote computer as described above. The device 1 can, by allowing computing device 4 to execute the interrogation protocol 9, interrogate the transducers 7 of a probe 6 in the correct order.

Preferably the computing device 4 has interrogation protocols 9 for at least two types of different probes 6, but suitably it can have interrogation protocols 9 for 3, 5, 8, 12, 20, 50 or more different probes 6. For each probe 6 the interrogation protocol 9 specifies, at least the order in which the transmitter/receiver circuits 3 shall send and receive voltage pulses in order to determine the parameters for each of the transducer elements 3 and leads 8 as described above. The interrogation protocol 9 can also provide information to the control device 2 which is useful for carrying out the interrogation. This may include information about the number of transducer elements 7 present in the probe 6 to be tested, which frequency to use, which voltage to use, the geometric arrangement of the transducer elements in the probe and the physical dimension of the piezoelectric crystal of the transducer element (which can be, for example, from 0.1 mm to 0.7 mm).

The user choses interrogation protocol 9 depending on which type of probe 6 he is testing, and the computing device 4 uses the chosen interrogation protocol 9 to send signals via rest of control device 2 to activate the transmitter/receiver circuits 3 in the order determined by the interrogation protocol 9 and to carry out the tests of the interrogation mode.

Alternatively, the device 1 may be used, in the image mode, to create an ultrasound image for purposes of testing the probe 6. The control device 2 together with the computing device 4 is capable of generating an image by methods known in the art. Thus, the control device 2 and the computing device 4 may send instruction signals to multiple or all transmitter/receiver circuits 3 simultaneously or almost simultaneously to simultaneously or almost simultaneously ("almost simultaneously" refers to up to 40 microseconds) activate a subset or all transducers in order to create an image.

This enables the production of images in real time during probe testing. In order to create a real time image the image has to be updated at least 4 times per second, preferably at least 5 times per second or more often. Otherwise the human eye does not perceive the image as a real time image. Previous devices for testing ultrasound probes has only one transmitter/receiver and switches between different transducers with the aid of relays, which is far too slow to create a real time image. In order to obtain a real time image with suitable resolution that updates 5 times per second the pulse repetition frequency (PRF) should be at least 640 Hz if there is 128 transmitter/receivers.

Creating a real time image is useful for checking that the ultrasound probe really works as intended and that it produces a useful image. The image mode may be a Doppler image mode. Doppler imaging mode enables the detection of relative motion. For this purpose a phantom target 22 with moving parts may be used. Doppler mode has the advantage that statistical methods are used to amplify the signal, making it possible to obtain more specific information about the probe.

Doppler mode may also be used for checking that a subset of transducers 7 works as intended. The device can be set to receive only in Doppler mode in order to obtain specific information about a certain transducer element.

The real time image can also be used to verify the results from the transducer interrogation mode. Additional information about the character of a detected error can be obtained by setting the device to B-mode (Brightness mode) or Doppler mode.

Also, the user may use the real time image mode for testing for faults in the leads 8 by watching the image and simultaneously pressing and/or moving different parts of the cord with his hands. If the fault comes and goes as he moves the lead 8, it is likely that there is some fault in the lead 8.

FIG. 2 is an example of a device 1. For the creation of images, the computing device 4 includes or is attached to a scan converter 10 or a frame grabber for generating an image. A live image can be displayed on the display 11. The scan converter 10 suitably has a frequency that allows the display of a live image, thus suitably it has a frequency of higher than 5 Hz. The display 11 can be a display of the kind normally connected to personal computers, for example a LCD display.

Testing is conveniently done with a phantom ultrasound target 22, a target that is specially designed to provide reflections of ultrasound waves in a predictable manner. The arrows from the probe in FIG. 2 indicate ultrasound pulses and echoes.

The device 1 may be connectable or include an adapter 20 which enables the connection of device 1 to different types of probes 6 trough connector of probe 25. Normally a probe 6 comprises of a number of transducers elements for example 128 transducer elements 7, each with one lead 8. The leads 8 are connectable to the ultrasound transmitter machine through a connector of probe 25. The physical shape of the connector of probe 25 can sometimes vary between manufacturers. Also, even if the probes from two different manufactures have the same type of physical connection they may have different wiring. The probe connector of probe 25 may provide contacts for, for example, power supply and earth on different positions on the connector of probe 25. For example in one manufacturer, power supply may be on contact pin number 3 of the connector of probe 25 and earth on contact pin number 27, whereas in the probe of another manufacturer, power may be on pin number 7 and earth on pin number 4. Adapter 20 ensures that for example power and earth connections to the probe 6, which are difficult or impossible to code by interrogation protocol 9, are correct. For this reason, different adapters 20 may have to be used for different types of probes 6. The interrogation protocol 9 may comprise information about which adapter 20 that should be used for a certain type of probe 6. This information may be provided to the user, so that he or she can attach the correct adapter 20. For example this information can be provided through a user interface, for example on display 11. For example, a dialog box may be provided on display 11, the dialog box displaying a message about which adapter 20 to attach. Preferably this information is displayed to the user before the test starts.

The device 1 may be capable of producing a report after conclusion of the test of the probe 6. The report may be a digital document in a format that is readable by a computing device. For example it may be a digital document in .pdf- or .doc format. Suitably the report includes at least one of the following information points for each transducer: pulse spectrum with the highest and the lowest capacitance ($\Omega$), frequency (Hz), central frequency (Hz), bandwidth (Hz), pulse width (s), relative sensitivity, analog pulse, element gain and crosstalk.

Today most probes have 128 transducers or more which enables the production of high quality images. Suitably the device 1 has a high number of transmitter/receiver circuits 3 to at least match the number of transducers, suitably at least 128 transmitter/receiver circuits to accommodate the most frequently occurring ultrasound probes.

Figure 3:
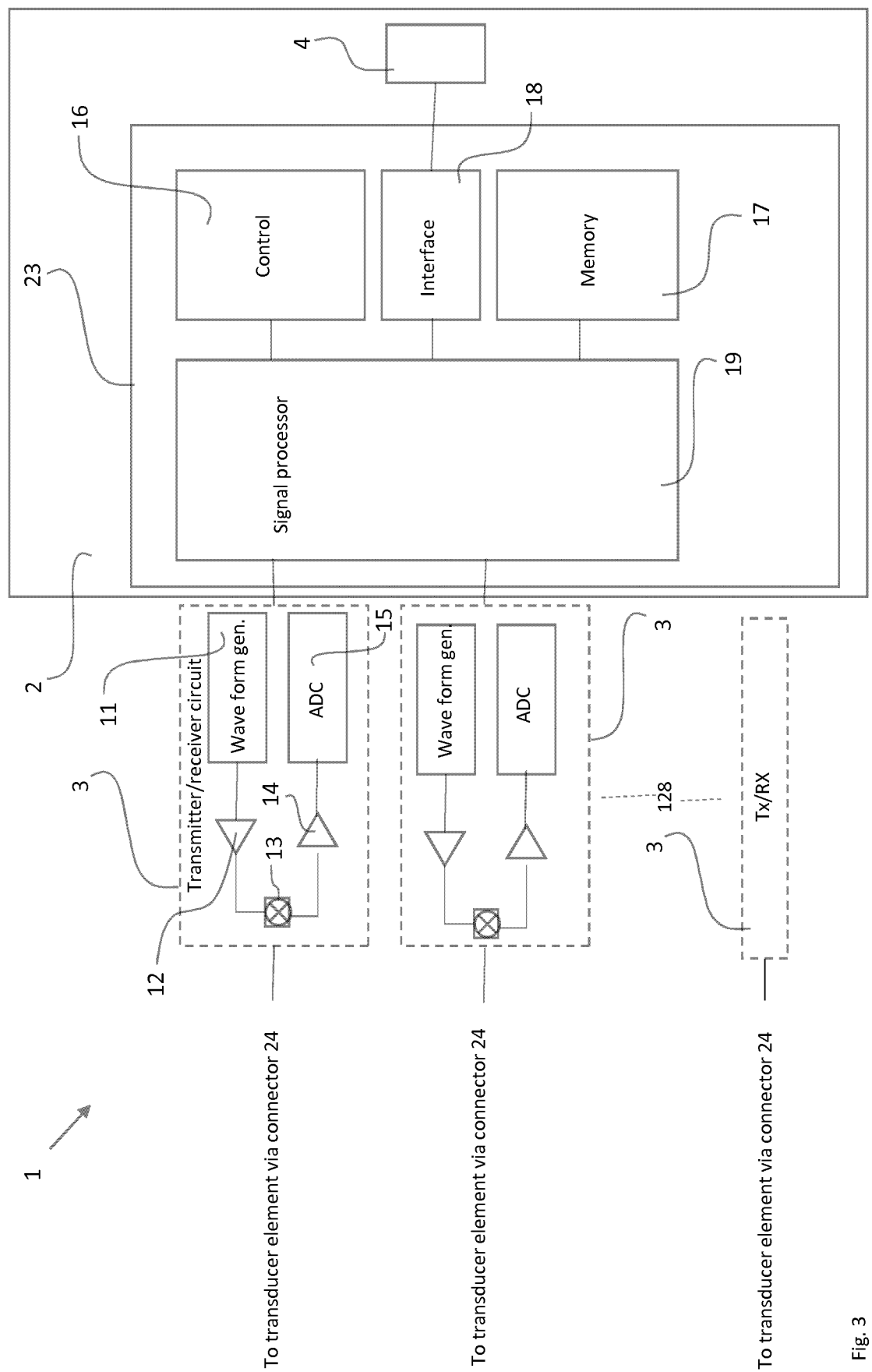
FIG. 3-4 are examples of circuits that can be used in the device.

An example of a device 1 with 128 transmitter/receiver circuits 3 is shown in more detail in FIG. 3. The transmitter/receiver circuits 3 are under control of a control device 2. Here control device 2 consists of a processing circuit 23 and computing device 4. Each transmitter/receiver circuit 3 represents one channel, the number of transmitter/receiver circuits being equal to the number of channels in this figure.

Each transmitter/receiver circuit 3 comprises a wave form generator 11, an amplifier 12, a TR switch 13, a receiver 14 and an analog to digital converter (ADC) 15.

The processing circuit 23 of control device 2 can comprise a control circuit 16 which runs on firmware stored on memory 17. Interface 18 receives and sends digital signals to computing device 4. The interface 18 receives instructions from computing device 4 and transfers this to the rest of processing circuit 23. Signal processor 19 may be used to analyze the received signals during the interrogation tests. Signal processor 19 may provide means for Doppler mode imaging.

Control device 2 receives digitalized signals from the ADC 15 of each transmitter/receiver circuit 3 and processes this signal. Signal processing can be carried out by software in computing device 4.

Figure 4:
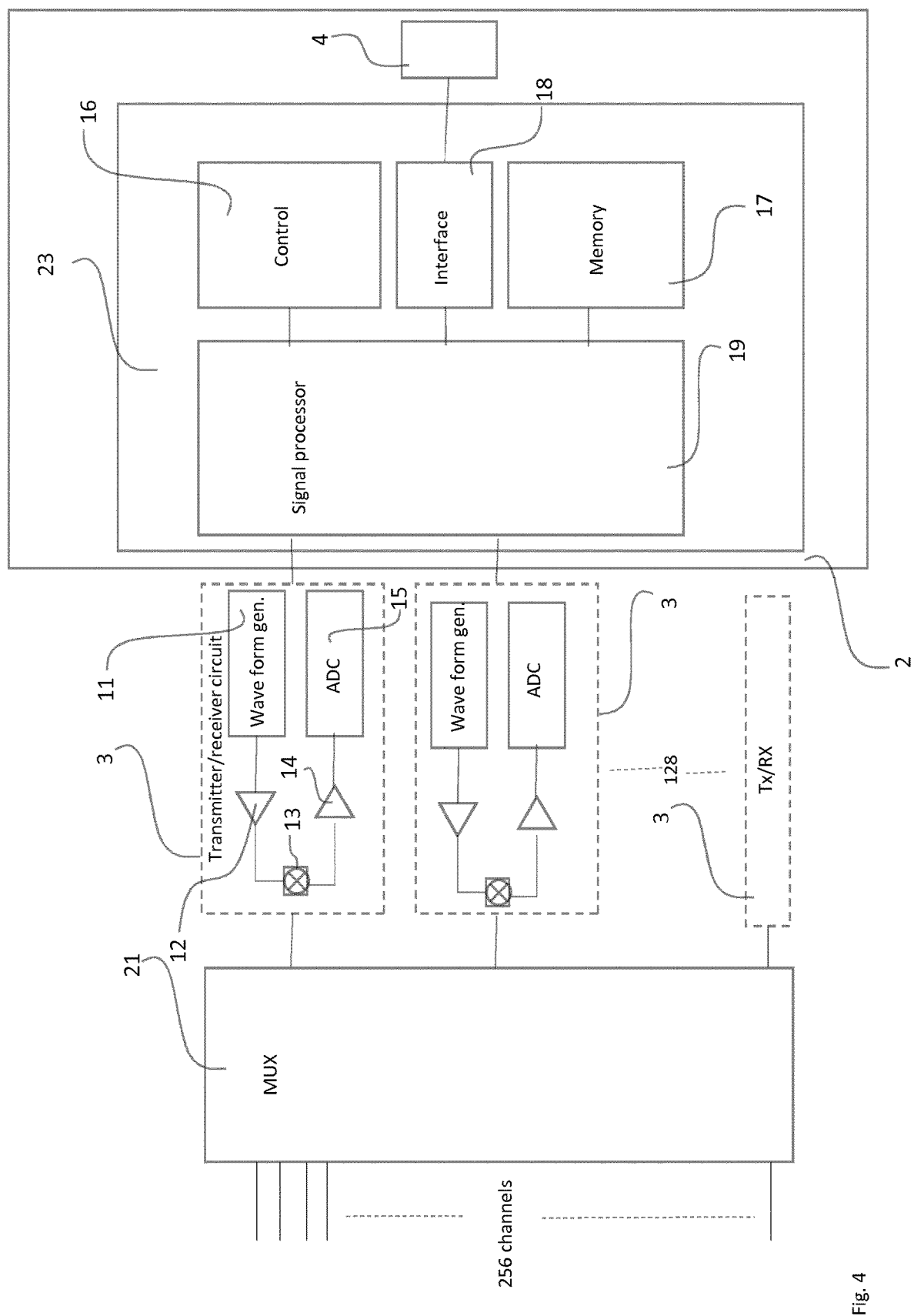

The device 1 is a multichannel device such that it has enough channels to create an image, preferably a real time image when the probe 6 is capable of doing so. Suitably the number of channels correspond to the number of transducers 7 in the probe that is being tested. Most probes has 128 transducers 7 and thus the device preferably has at least 128 channels. Even more preferably it has more than 256 channels.

Where the number of transducers in the probe 6 being tested is greater than the number of channels in the device 1, a multiplexing device (MUX) can be used. The device with a MUX 21 is shown in FIG. 4 and FIG. 2. MUX 21 can for example be used to obtain a useful real time image from a probe with 256 or more transducing elements 7 when the device 1 has 128 transmitter/receiver circuits 3. A MUX 21 suitably receives voltage pulses to and from the channels and routes them to and from the 256 transducers at certain intervals, such that one channel (transmitter/receiver 3) can serve two different transducers.

Yet another advantage with the device 1 is that crosstalk between the leads 8 or even between transducing elements 7, can be detected without time-consuming recursions.

Normally each lead 8 in the cord of the probe is shielded such that voltage in one lead 8 does not induce voltage in a neighboring lead 8. However, the shielding is prone to damage, which may lead to crosstalk between transducers 7 and/or leads 8. An example of crosstalk is that a signal is sent on channel 14 only, but a signal is received on channel 27 as well (besides channel 14). This often occurs as subtle irregularities in a live ultrasound image, and is difficult to diagnose.

Figure 5B:
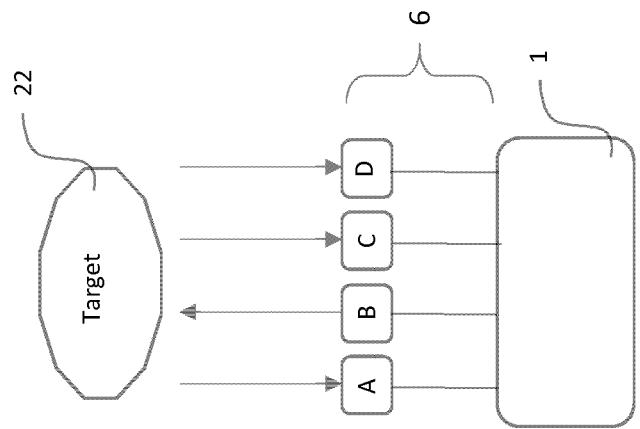
FIG. 5-6 show a method for detecting crosstalk in a probe.
Figure 5A:
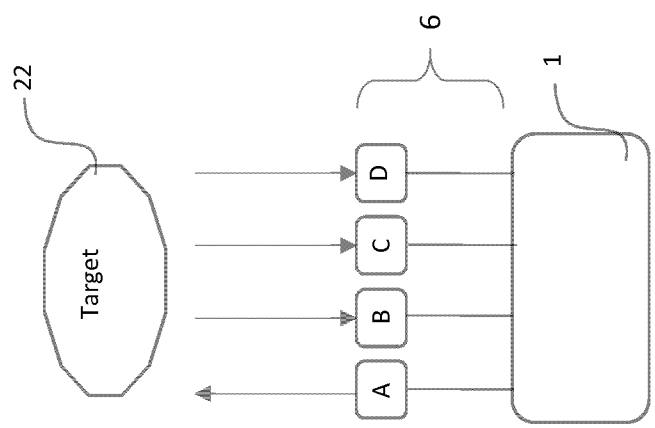

The inventive device can test for crosstalk in the leads 8 and/or transducers 7 of a ultrasound probe 6 in the following manner, as shown in FIGS. 5*a* and 5*b* which schematically shows testing of a schematic probe with four transducing elements A, B, C and D. Arrows pointing upwards in these figures indicate that the transducer 7 is receiving a voltage pulse and is sending an ultrasound pulse; and arrows pointing downwards indicate that the transducer 7 is set to receive an ultrasound pulse, or more accurately the receiver 3 of that transducer 7 is set to receive an voltage pulse from its transducing element 7. With reference to FIG. 5a a voltage pulse is first sent from device 1 to a first transducer/lead pair, in this case transducer A, to activate that transducer 7 of the probe 6. The device 1 is set to receive voltage pulses from the other transducer/lead pairs, in this case transducers B, C and D. Those transducer/lead pairs that have crosstalk with the transducer/lead pair receiving the voltage pulse, in this case transducer A/channel A, will get a response, because the voltage pulse induced a signal in those leads. If a signal is received from B, C or D there is crosstalk from this channel/transducer. For example, if a signal is received from transducer C there is crosstalk from A to C. When one transducer has been interrogated for crosstalk in this manner another (previously not interrogated) transducer is selected for interrogation. In this example, when transducer A has been interrogated for crosstalk, transducer B is interrogated for crosstalk in the same manner as shown in FIG. 5b. Device 1 is then set to receive from transducers A, C and D. The process is carried on until crosstalk from all transduces A, B, C and D has been checked.

Thus, if the device has 128 channels, transmission is first carried out on channel 1, channels 2-128 are set to receive. The other channels 2-128 can be tested in the same manner.

Testing a 128 channel probe with a one channel device would take much longer time since it would require a recursive operation and necessary to send 127 pulses for testing for crosstalk for each transducer. Also, crosstalk detection requires that receiving starts within about 100 ns of transmission, and a relay, which is mechanical, is much too slow for this.

FIGS. 5a and 5b shows a phantom target 22. However such a phantom target 22 may not be necessary since often crosstalk can be detected without the creation of a sound pulse, since crosstalk usually is caused by short circuits in the probe 6.

Figure 6:
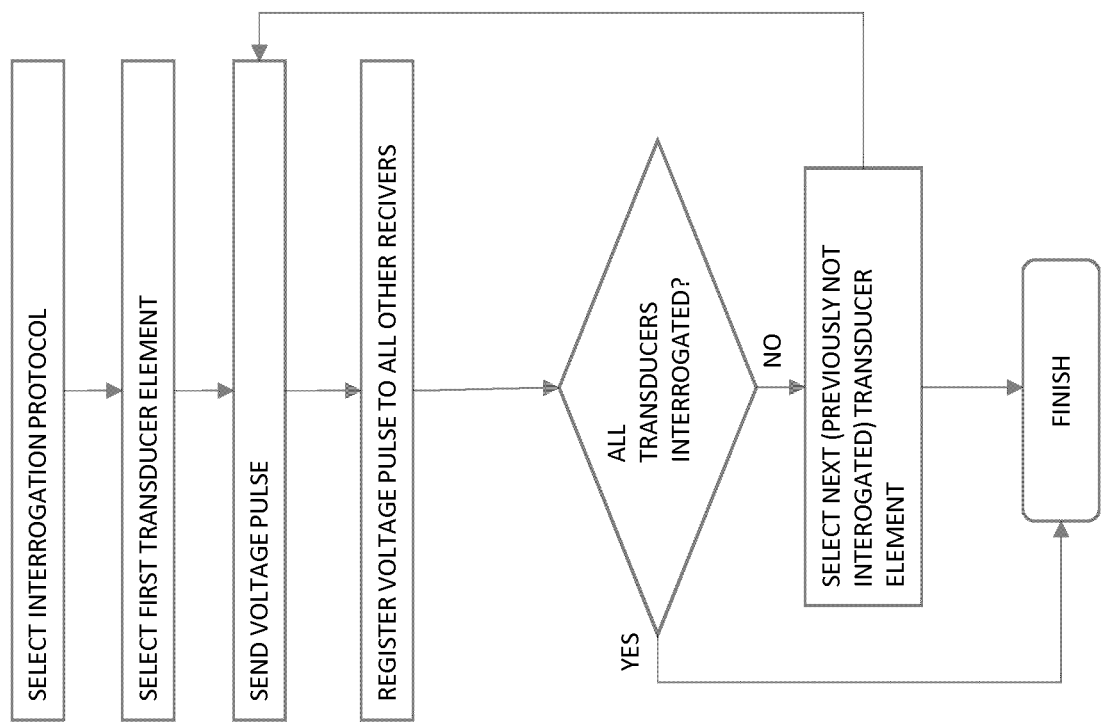

FIG. 6 shows the method for detecting crosstalk as a flow chart. The method may comprise the step of before the test starts, to display information to the user about which type of adapter 20 that should be used for connecting the probe 6 to the device 1.

The invention claimed is:

1. A method of testing an ultrasound probe having a plurality of transducer element/lead pairs, the method comprising:
   selecting an interrogation protocol from a plurality of interrogation protocols, each of the plurality of interrogation protocols specifying an order in which voltage pulses are sent from transmitters of a plurality of transmitter/receiver circuits to the plurality of transducer element/lead pairs;
   sending voltage pulses according to the selected interrogation protocol; and
   registering voltage pulses received by receivers of the plurality of transmitter/receiver circuits according to the selected interrogation protocol,
   the selected interrogation protocol detecting crosstalk between any two transducer element/lead pairs of the plurality of transducer element/lead pairs by:
   i. selecting an individual transducer element/lead pair of the plurality of transducer element/lead pairs,
   ii. sending a voltage pulse to the individual transducer element/lead pair,
   iii. registering voltage pulses received by each of the receivers of the plurality of transmitter/receiver circuits,
   iv. repeating i)-iii) until a voltage pulse is sent to each individual transducer element/lead pair, and
   v. producing a report of detected crosstalk based on results from i) to iv).

2. The method according to claim 1, further comprising:
   determining at least one of the following parameters for each of the plurality of transducer element/lead pairs:
   capacitance,
   frequency,
   bandwidth,
   pulse width, and
   relative sensitivity.

3. The method according to claim 1, further comprising:
   displaying information on a display to a user about an adapter that is to be connected to a tested ultrasound probe, the displayed information being stored in the selected interrogation protocol.

4. The method according to claim 1, wherein each of the plurality of interrogation protocols corresponds to a different type of ultrasound probe.

* * * * *

UNITED STATES PATENT AND TRADEMARK OFFICE
CERTIFICATE OF CORRECTION

PATENT NO. : 10,509,014 B2  
APPLICATION NO. : 15/119836  
DATED : December 17, 2019  
INVENTOR(S) : Björn Segall Page 1 of 1

It is certified that error appears in the above-identified patent and that said Letters Patent is hereby corrected as shown below:

On the Title Page

In item (73) Assignee, please replace:
"BBS FÖRSÄLININGS AB" with -- BBS FÖRSÄLJNINGS AB --.

Signed and Sealed this
Twenty-eighth Day of January, 2020

Andrei Iancu
*Director of the United States Patent and Trademark Office*